United States Patent [19]
Atkinson et al.

[11] Patent Number: 5,454,784
[45] Date of Patent: Oct. 3, 1995

[54] CONTROL VALVE FOR A FLUID SET

[75] Inventors: Robert W. Atkinson, Dover; Kim R. Harmon, Mineral City, both of Ohio

[73] Assignee: Zimmer, Inc., Warsaw, Ind.

[21] Appl. No.: 259,756

[22] Filed: Jun. 10, 1994

[51] Int. Cl.[6] .................................................. A61M 1/00
[52] U.S. Cl. ........................ 604/31; 604/30; 137/115
[58] Field of Search ........................... 604/30, 290, 323, 604/325, 326, 335, 31, 34, 50, 33; 137/87, 115, 625.2, 625.6, 625.25, 625.26, 594–596, 596.12, 596.13, 596.14

[56] References Cited

U.S. PATENT DOCUMENTS

| | | | |
|---|---|---|---|
| 1,847,954 | 3/1932 | Fisher | 604/30 X |
| 2,832,341 | 4/1958 | Stack | 604/30 X |
| 3,056,575 | 10/1962 | Mooney | 251/172 |
| 3,358,677 | 12/1967 | Sheldon | 128/24 |
| 3,657,893 | 4/1972 | Tadokoro et al. | 60/289 |
| 3,831,821 | 8/1974 | Doyen | 222/255 |
| 3,889,675 | 6/1975 | Stewart | 128/240 |
| 3,900,022 | 8/1975 | Widran | 128/7 |
| 3,903,923 | 9/1975 | Loup et al. | 137/539.5 |
| 3,943,969 | 3/1976 | Rubin et al. | 137/538 |
| 4,237,880 | 12/1980 | Genese | 128/214 |
| 4,258,721 | 3/1981 | Parent et al. | 128/747 |
| 4,265,271 | 5/1981 | Rosaen et al. | 137/540 |
| 4,413,645 | 11/1983 | Seabase et al. | 137/223 |
| 4,431,019 | 2/1984 | Kopp et al. | 137/87 |
| 4,535,818 | 8/1985 | Duncan et al. | 137/846 |
| 4,555,645 | 11/1985 | Atkinson | 310/27 |
| 4,561,431 | 12/1985 | Atkinson | 128/66 |
| 4,604,089 | 8/1986 | Santangelo et al. | 604/30 |
| 4,635,621 | 1/1987 | Atkinson | 128/66 |
| 4,650,461 | 3/1987 | Woods | 604/28 |
| 4,650,462 | 3/1987 | DeSatnick et al. | 604/30 |
| 4,662,871 | 5/1987 | Rafelson | 604/119 |
| 4,671,786 | 6/1987 | Krug | 604/4 |
| 4,795,424 | 1/1989 | Burner | 604/30 |
| 4,820,265 | 4/1989 | DeSatnick et al. | 604/30 |
| 4,940,457 | 7/1990 | Olson | 604/30 |
| 4,998,527 | 3/1991 | Meyer | 128/6 |
| 4,998,914 | 3/1991 | Wiest et al. | 604/67 |
| 5,100,377 | 3/1992 | Freitas et al. | 604/30 |
| 5,152,746 | 10/1992 | Atkinson et al. | 604/31 |
| 5,178,606 | 1/1993 | Ognier et al. | 604/31 |
| 5,205,834 | 4/1993 | Moorehead et al. | 604/247 |

FOREIGN PATENT DOCUMENTS

WO86/00534  1/1986  WIPO ........................... A61M 1/00

OTHER PUBLICATIONS

3M Brochure—3M Arthroscopy Pump—No date available.
Brochure—Journal of Arthroscopic and Related Surgery—"Intra–Articular Pressures During Arthroscopic Knee Surgery"—1986.

Primary Examiner—C. Fred Rosenbaum
Assistant Examiner—Bryan L. Tsosie
Attorney, Agent, or Firm—Cary R. Reeves

[57] ABSTRACT

An irrigation system contains a safety relief valve and a safety relief valve control valve. The safety relief valve control valve acts to modulate the operation of the safety relief valve when there is flow from an outflow port. By this mechanism high flow rates are accommodated without causing premature activation of the safety relief valve.

10 Claims, 2 Drawing Sheets

CONTROL VALVE FOR A FLUID SET

BACKGROUND OF THE INVENTION

The present invention relates to irrigation systems for communicating fluid to a surgical site within a body. More specifically it relates to irrigation systems having a valve arrangement capable of safely pressurizing the surgical site under a wide range of flow conditions.

Surgery on interior portions of the body are increasingly often being performed with the aid of endoscopic techniques. In such procedures, a scope cannula is inserted into the body to provide access to the surgical site. An endoscope is inserted into the scope cannula which allows viewing of the surgical site. Surgery is performed with instruments passed through an adjacent cannula or in some instances through the scope cannula or in still other instances through the endoscope itself. In order to facilitate the viewing of the surgical site and the use of the instruments, the tissues surrounding the surgical site are distended by fluid pressure. Typically the scope cannula comprises a dual lumen cannula having an inflow port connected to a first lumen for conducting fluid from a pump to the surgical site and an outflow port connected to a second lumen for conducting fluid away from the surgical site. By these means, a fluid flow loop is established consisting of fluid flowing from the pump through the inflow port, through the first lumen of the scope cannula into the surgical site, and then from the surgical site through the second lumen of the scope cannula and out the outflow port.

In order to distend the surgical site, more fluid is pumped into the surgical site than is allowed to drain from it thereby producing a positive distension pressure at the surgical site. Once a desired pressure is achieved, it is maintained by pumping fluid into the surgical site at the same rate that fluid leaves the surgical site. In practice, this is accomplished by modulating the pump output in order to control a pressure measured at a particular location in the fluid flow circuit.

An exemplary irrigation system is taught in U.S. Pat. No. 5,152,746 wherein a monitor line communicates the fluid pressure within the scope to a pump controller to modulate the pump to maintain the pressure within desirable and safe limits. For added safety, a safety relief valve is included in communication with the inflow line between the pump and the inflow port. When the pressure at the safety relief valve exceeds a safety relief valve activation pressure, the safety relief valve operates to discharge fluid to lower the pressure in the inflow line.

In use, the surgeon may desire to vary the amount of flow through the fluid circuit to accomplish different purposes. In one situation he may stop the outflow from the circuit in order to avoid agitation of the tissues being examined or to preserve the irrigation fluid being used. He may also wish to limit the amount of discharged fluid that must be disposed of. This situation is referred to as a static condition. The pump operates only to replenish the small amount of fluid which inevitably leaks from the circuit but there is little flow through the circuit. In the static condition, the pressure throughout the circuit is equal and therefore the pressure at the safety relief valve is equal to the pressure at the surgical site.

In another situation, the surgeon may want full flow through the circuit in order to actively flush away debris generated by the surgical procedure in order to cleanse the surgical site and facilitate his view through the scope. In this condition, or flow condition, the outflow port is fully open and the pump operates to replenish the fluid that flows through the outflow port and thereby maintain the desired distension pressure. The maximum flow through the system, for a predetermined distension pressure, will occur when the outflow port is fully open.

However, in the flow condition, the pressure measured at two points in the fluid circuit will be different. The difference, or back pressure, represents the incremental pressure required to overcome frictional resistance to the fluid flowing from the first point in the circuit to the second point in the circuit. Back pressure generally increases with increasing circuit length, decreasing tubing diameter, and increasing flow rate among other factors. When there is no flow there is no back pressure and the pressure at the two measurement points will be the same. When there is flow there will be back pressure. Therefore, in the flow condition, the pressure at the safety relief valve will be greater than the pressure at the surgical site. The difference is the back pressure which results from the fluid circuit geometry and the flow rate.

For prior art systems, this back pressure prevents the system from achieving the maximum safe pressure at the surgical site in the flow condition and thus prevents optimal distension. This is because the safety relief valve activation pressure must be set at the maximum safe pressure for the surgical site in order to protect the patient in the static condition. In the flow condition, back pressure causes the safety relief valve to reach its activation pressure before the surgical site reaches the maximum safe pressure. This effect, lowering of the maximum achievable distension pressure, increases as the flow rate through the circuit increases.

SUMMARY OF THE INVENTION

The invention of this disclosure provides an irrigation system in which high flow rates are achieved without causing premature activation of the safety relief valve. This result is achieved by providing within the circuit a safety relief valve control valve which acts to modulate the operation of the safety relief valve when there is flow from the outflow port.

DETAILED DESCRIPTION OF THE INVENTION

Figure 1:
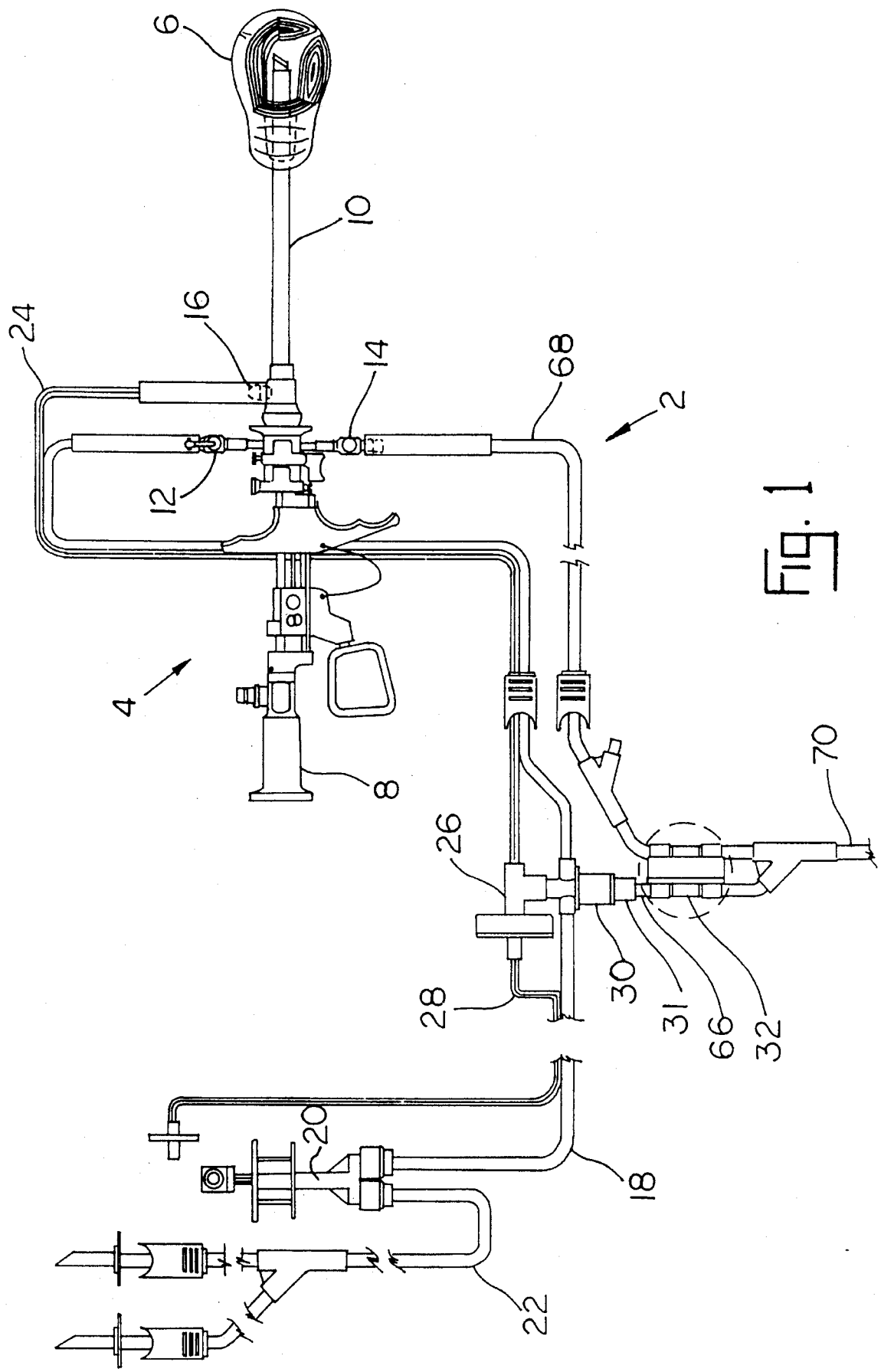
FIG. 1 is a schematic diagram of the fluid set of the present invention connected to a fluid pump and an endoscope.

Referring to FIG. 1, a fluid set 2 for connecting a pump to an endoscope comprises a set of tubes, connectors and valves. For exemplary purposes, an endoscope assembly 4 configured for performing electrocautery oblation on a human uterus 6 is shown. The endoscope assembly 4 includes an endoscope 8 and a cannula 10. The cannula 10 includes an inflow port 12, an outflow port 14, and a monitor port 16. An inflow line 18 connects the inflow port 12 to a pump 20. Preferably the pump 20 comprises a disposable member, connectable to a pump motor (not shown), that is incorporated into the fluid set 2 as shown. A supply line 22 connects the pump 20 to a supply of irrigation fluid. A wet monitor line 24 connects the monitor port 16 to a monitor diaphragm housing 26. A dry monitor line 28 leads from the monitor diaphragm housing 26 and is connectable to a pump motor controller (not shown). A safety relief valve 30, or SRV, is in fluid communication with the inflow line 18 and acts to discharge fluid through a discharge port 31 when the pressure in the inflow line 18 exceeds a predetermined activation pressure. The SRV preferably comprises a mechanical poppet valve having a poppet biased against a valve seat by a spring. The spring and valve seat geometry are designed to cause the valve to open when the fluid pressure on the poppet reaches the predetermined activation pressure. The function of this fluid circuit has been described in U.S. Pat. No. 5,152,746 and has been summarized in the background of the present disclosure.

Figure 2:
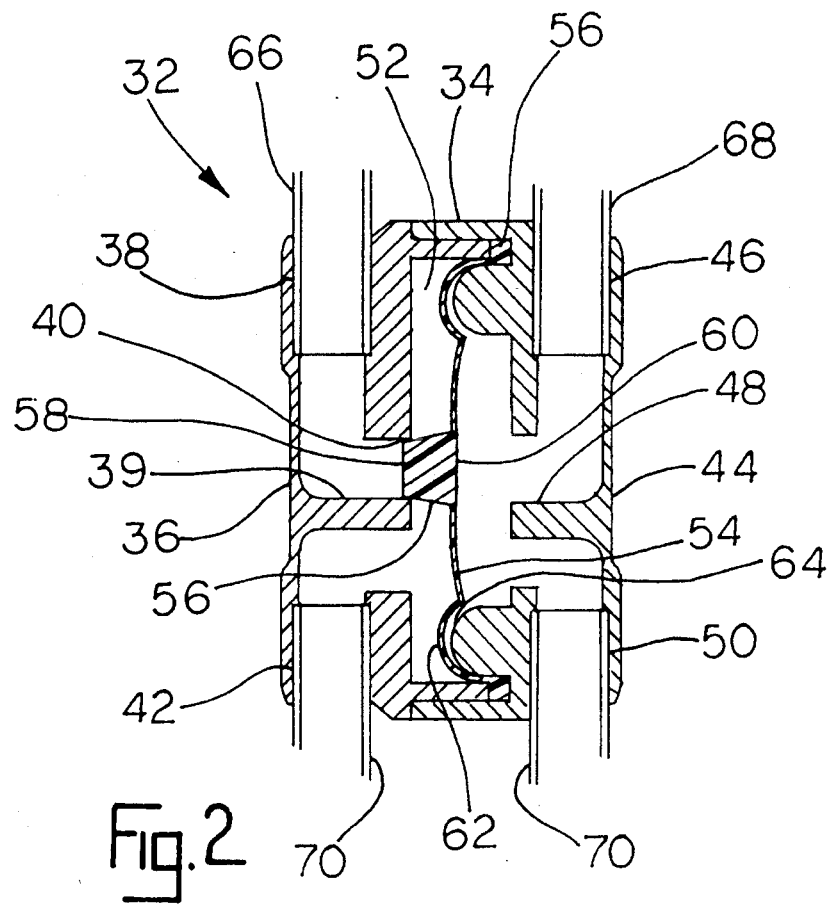
FIG. 2 is a sectional view of the safety relief valve control valve of the fluid set of the present invention in the flow condition.

The present invention advantageously includes a safety relief valve control valve 32, or SRVCV, to prevent the premature operation of the SRV 30, due to back pressure, when there is flow from the outflow port 14. Referring to FIG. 2, the SRVCV 32 comprises a housing 34. The housing 34 includes an SRV discharge side 36 defining a fluid passageway through the housing comprising an inlet 38, a fluid diverting bend 39, a plug seat 40, and an outlet 42. The housing 34 also includes a cannula outflow side 44 defining a fluid passageway through the housing comprising an inlet 46, a fluid diverting bend 48 and an outlet 50. Preferably, the fluid diverting bends 39 and 48 each divert fluid through approximately 90 degrees and the bends are in alignment with one another so that fluid traveling through the SRV discharge side 36 is directed toward the cannula outflow side 44 and vice versa.

The housing 34 further includes a chamber 52 disposed between the SRV discharge side 36 and the cannula outflow side 44. A diaphragm 54 is mounted in the housing 34 within the chamber 52 and forms a fluid tight divider between the fluid passageway in the SRV discharge side 36 and the fluid passageway in the cannula outflow side 44. In the preferred embodiment, the diaphragm 54 is a circular membrane formed of an elastomeric material and is attached to the housing 34 along the periphery 56 of the diaphragm. The diaphragm 54 carries a plug 56, having a plug face 58, on the side of the diaphragm 54 toward the SRV discharge side 36 of the housing 34. The plug face 58 aligns with the plug seat 40. The plug face 58 is smaller than the plug seat 40 so that when the diaphragm 54 is displaced toward the SRV discharge side 36 the plug 56 will seat in the plug seat 40 and prevent fluid flow through the passageway in the SRV discharge side 36 of the housing 34.

Preferably the plug face 58 is smaller than the cannula outflow side of the diaphragm 60. This creates a mechanical advantage equal to the ratio of the area of the outflow side of the diaphragm 60 to the area of the plug face 58 when the plug 56 is seated in the plug seat 40. Because of this mechanical advantage, relatively low pressures on the cannula outflow side of the diaphragm 60 will tend to keep the plug 56 seated even when there are relatively large pressures on the plug face 58.

Figure 3:
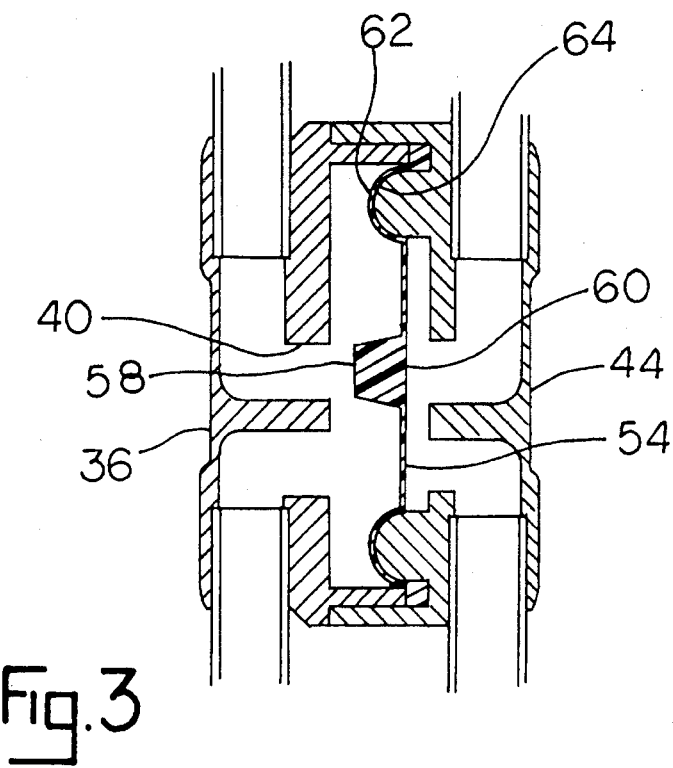
FIG. 3 is a sectional view of the safety relief valve control valve of the fluid set of the present invention in the static condition.

To dispose the diaphragm 54 to movement toward the SRV side 36, the diaphragm 54 preferably also has an annular ridge 62 which conforms to a supporting annular seat 64. As the diaphragm 54 is moved toward the cannula outflow side 44, the annular ridge 62 seats on the annular seat 64 thereby effectively shortening the radius of the diaphragm 54 which stiffens the diaphragm 54 thus resisting movement in that direction, as shown in FIG. 3. As the diaphragm is moved toward the SRV discharge side the annular ridge 62 moves away from the annular seat 64 thereby effectively lengthening the radius of the diaphragm 54 which causes the diaphragm 54 to be less stiff thus facilitating movement in this direction, as shown in FIG. 2. Therefore the diaphragm 54 tends to move toward the SRV side 36 and seat the plug 56 when there is flow on the cannula outflow side 44. Yet, when the SRV 30 activates and there is flow through the SRV side 36, the diaphragm resists moving toward the cannula outflow side 44. Therefore both of the fluid passageways are left open for drainage when the SRV 30 activates.

An SRV discharge line 66 connects the SRV discharge port 31 to the inlet 38 of the SRV discharge side 36 of the SRVCV 32. An outflow line 68 connects the outflow port 14 of the cannula 10 to the inlet 46 of the cannula outflow side 44 of the SRVCV 32. The outlets 42 and 50 are connected to a common drain line 70.

In use, the SRVCV 32 operates to prevent premature discharge by the SRV 30 due to back pressure in the flow condition. The SRV 30 is designed to activate near the maximum safe pressure of the surgical site 6. In the static condition there is no back pressure and the fluid pressure at the SRV 30 is the same as the fluid pressure at the surgical site 6. Therefore the SRV 30 will only operate to discharge fluid when the maximum safe pressure is exceeded at the surgical site 6.

During a flow condition however, the pressure seen at the SRV 30 is greater than the pressure at the surgical site 6 due to back pressure. Therefore the SRV 30, absent the SRVCV 32, would operate when the surgical site pressure is below the maximum safe level and prevent the system from achieving the desired distension pressure. However, in the present invention, flow through the outflow line 68 is directed through the SRVCV 32. The outflow causes the diaphragm 54 to move toward the SRV discharge side 36 of the SRVCV 32 causing the plug 56 to seat. With the plug 56 seated, the discharge path of the SRV 30 is blocked and the SRV 30 cannot open until the pressure at the SRV 30 is equal to the pressure necessary to dislodge the plug 56. The mechanical advantage of the outflow side of the diaphragm 60 over the plug face 58 is such that the pressure to dislodge the plug 56 is equal to the SRV 30 activation pressure plus the back pressure at the SRV 30. The operation of the SRVCV 32 is proportional to the amount of flow through the SRVCV 32 on the outflow side 44. Therefore, the pressure required to dislodge the plug 56 increases with the back pressure at the SRV 30 since both are functions of the flow rate of fluid in the fluid set 2. It has been found that a mechanical advantage of 40.5:1 works particularly well. In a typical flow condition there is a pressure on the cannula outflow side of the diaphragm 60 of approximately 3–4 mmhg and therefore a pressure of approximately 121–162 mmhg is required on the plug face 58 to dislodge the plug 56 and discharge fluid through the SRV 30.

The SRVCV 32 effectively cancels the effect of back pressure on the SRV 30. In the static condition and very low flow conditions, the SRV 30 works normally to limit the pressure at the surgical site 6 in a pump malfunction situation. In normal to high flow conditions, the SRVCV 32 operates through the action of the SRVCV diaphragm 54 to proportionally raise the pressure required for the SRV 30 to operate thereby effectively canceling the effects of back pressure at the SRV 30.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. A fluid set for connection to a fluid source and a surgical site, the fluid set comprising:

first means for communicating fluid from the fluid source to the surgical site;

second means for communicating fluid from the surgical site;

relief means in fluid communication with the first means;

a discharge port in fluid communication with the relief means, the relief means operating to divert fluid from the first means to the discharge port to relieve a fluid pressure in the first means when the fluid pressure in the first means reaches a predetermined pressure; and control means in fluid communication with the discharge port and the second means, the control means being responsive to a predetermined rate of fluid flow through the second means to prevent the relief means from operating at the predetermined pressure.

2. A fluid set for connection to a fluid source and a surgical site, the fluid set comprising:

first means for communicating fluid from the fluid source to the surgical site;

second means for communicating fluid from the surgical site;

relief means in fluid communication with the first means;

a discharge port in fluid communication with the relief means, the relief means operating to divert fluid from the first means to the discharge port to relieve a fluid pressure in the first means when the fluid pressure in the first means reaches a predetermined pressure; and control means in fluid communication with the discharge port and the second means, the control means being responsive to a predetermined rate of fluid flow through the second means to prevent the relief means from operating at the predetermined pressure, the relief means comprising a pressure operated mechanical safety relief valve.

3. The fluid set of claim 2 wherein the control means comprises a mechanical control valve, the mechanical control valve comprising a housing having a first fluid passageway having an inlet and an outlet, the inlet in fluid communication with the discharge port; and a second fluid passageway having an inlet and an outlet, the inlet in fluid communication with the second means for communicating fluid from the surgical site.

4. The fluid set of claim 3 wherein the mechanical control valve further comprises a diaphragm mounted in the housing separating the first and second fluid passageways, the diaphragm moving toward the first fluid passageway in response to a predetermined rate of fluid flow through the second means, the diaphragm thus moved blocking fluid flow through the first fluid passageway such that the safety relief valve is prevented from operating at the predetermined pressure.

5. The fluid set of claim 4 wherein the mechanical control valve further comprises an annular ridge formed on the diaphragm and a corresponding annular seat formed in the housing adjacent the second fluid passageway, the seat being in contact with a side of the diaphragm exposed to fluid flow through the second fluid passageway, the annular ridge seating on the annular seat to resist motion of the diaphragm toward the second fluid passageway.

6. The fluid set of claim 4 wherein the mechanical control valve further comprises a plug carried by the diaphragm and a plug seat located in the first fluid passageway, the plug moving to seat in the plug seat when the diaphragm moves toward the first fluid passageway.

7. The fluid set of claim 6 wherein the plug has a plug face that fits within the plug seat and a side of the diaphragm exposed to fluid flow through the second fluid passageway is larger than the plug face.

8. The fluid set of claim 6 wherein a fluid pressure necessary to dislodge the plug from the plug seat and thereby enable the operation of the safety relief valve is proportional to the flow rate of fluid through the fluid set and further wherein the fluid pressure at the safety relief valve is greater than a fluid pressure at the surgical site, this difference between the fluid pressure at the safety relief valve and the fluid pressure at the surgical site being due to a back pressure which is proportional to the rate of flow of fluid through the fluid set such that the fluid pressure necessary to dislodge the plug from the plug seat prevents the safety relief valve from operating before the fluid pressure at the surgical site reaches the predetermined pressure.

9. The fluid set of claim 6 wherein there is a fluid pressure at the surgical site and a larger fluid pressure at the safety relief valve, the pressure at the safety relief valve being larger due to a back pressure, the back pressure being proportional to the rate of flow of fluid through the fluid set, and wherein there is a plug dislodging fluid pressure necessary to dislodge the plug from the plug seat and thus enable the operation of the safety relief valve which plug dislodging fluid pressure is also proportional to the flow rate of fluid through the fluid set, such that the fluid pressure necessary to dislodge the plug from the plug seat increases as the back pressure increases and thus prevents the safety relief valve from operating before the fluid pressure at the surgical site reaches the predetermined pressure.

10. A fluid set for connection to a pump and an through the outflow line.

* * * * *

UNITED STATES PATENT AND TRADEMARK OFFICE
CERTIFICATE OF CORRECTION

PATENT NO. : 5,454,784
DATED : October 3, 1995
INVENTOR(S) : Atkinson et al.

It is certified that error appears in the above-indentified patent and that said Letters Patent is hereby corrected as shown below:

Cancel "10. A fluid set for connection to a pump and an through the outflow line." in column 6, line 52, and insert the following claim:

-- 10. A fluid set for connection to a pump and an endoscope, the endoscope having inflow and outflow ports, the fluid set comprising:

an inflow line to communicate pressurized fluid from the pump to the inflow port;
    an outflow line to communicate fluid from the outflow port;
    a safety relief valve in fluid communication with the inflow line,
    a discharge port in fluid communication with the safety relief valve, the safety relief valve operating at a predetermined pressure in the inflow line to discharge fluid through the discharge port; and
    a control valve connected to both the discharge port and the outflow line, the control valve comprising
        a housing having a first fluid passageway having an inlet and an outlet, the inlet in fluid communication with the discharge port and a second fluid passageway having an inlet and an outlet, the inlet in fluid communication with the outflow line,
        a diaphragm mounted in the housing separating the first and second fluid passageways,
        a plug carried by the diaphragm, and
        a plug seat in the first fluid passageway, the diaphragm being movable toward the plug seat when fluid flows through the second fluid passageway such that the plug seats in the plug seat and prevents flow through the first fluid passageway and thus prevents the safety relief valve from operating when there is a predetermined rate of fluid flow through the outflow line.--

Signed and Sealed this

Sixteenth Day of January, 1996

Attest:

BRUCE LEHMAN

Attesting Officer

Commissioner of Patents and Trademarks